| United States Patent [19] | [11] Patent Number: 4,534,973 |
| Kim | [45] Date of Patent: Aug. 13, 1985 |

[54] PHARMACEUTICAL COMPOSITIONS

[75] Inventor: Miwon S. Kim, Princeton Junction, N.J.

[73] Assignee: Carter-Wallace, Inc., New York, N.Y.

[21] Appl. No.: 635,962

[22] Filed: Jul. 31, 1984

[51] Int. Cl.$^3$ .................. A61K 31/27; A61K 31/61
[52] U.S. Cl. .................................. 514/162; 514/479
[58] Field of Search .................... 424/300, 234, 260

[56] References Cited
PUBLICATIONS

Chem. Abst., vol. 89, 1978-12252j.

*Primary Examiner*—Stanley J. Friedman
*Attorney, Agent, or Firm*—Kevin B. Clarke

[57] ABSTRACT

Compositions for the relief of pain, muscle spasm and limited mobility associated with acute painful muscoloskeletal conditions are disclosed. Such compositions comprise in combination, a N-monosubstituted-2, 2-dialkyl-1, 3-propanediol dicarbamate and aspirin.

4 Claims, No Drawings

PHARMACEUTICAL COMPOSITIONS

This invention relates to novel pharmaceutical compositions. More particularly this invention relates to novel therapeutic compositions capable of relieving pain, muscle spasm and limited mobility associated with acute painful muscoloskeletal conditions in warm-blooded animals.

Specifically this invention relates to a therapeutic composition comprising:
a. N-monosubstituted-2,2-dialkyl-1,3-propanediol dicarbamates having structure:

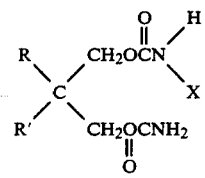

wherein R is selected from the group consisting of methyl and ethyl, R' is selected from the group consisting of ethyl, propyly, isopropyl, butyl and isobutyl and X is selected from the group consisting of ethyl, propyl, isopropyl, butyl, isobutyl and allyl;
b. and aspirin.

The N-monosubstituted-2,2-dialkyl-1,3-propanediol dicarbamates, particularly the N-isopropyl-2-methyl-2-propyl-1,3-propanediol dicarbamate known as carisoprodol are disclosed in U.S. Pat. No. 2,937,119 and are colorless liquids of high boiling point or low melting solids. They are soluble in most organic solvents but only slightly soluble in water at room temperature. The N-monosubstituted-2,2-dialkyl-1,3-propanediol dicarbamates possess strong muscle relaxant activity. The N-monosubstituted-2,2-dialkyl-1,3-propanediol dicarbamates, particularly carisoprodol are centrally-acting muscle relaxants that do not directly relax the tense skeletal muscles in warm-blooded animals. In animal studies carisoprodol has been shown to produce muscle relaxation by blocking interneuronal activity and depressing the transmission of polysynaptic neurons in the spinal cord and in the decending reticular formation of the brain.

In man, the mode of action of carisoprodol has not been clearly identified but is believed to be related to its sedative properties. When ingested in tablet form, the onset of the muscle relaxant properties of the N-monosubstituted-2,2-dialkyl-1,3-propanediol dicarbamates is rapid and its effects last for from four to six hours.

Aspirin chemically described as 2-(acetyloxy)benzoic acid or salicylic acid acetate or acetylsalicylic acid is a non-narcotic analgesic having anti-flammatory and antipyretic activity. Aspirin is the standard non-narcotic analgesic against which all other non-narcotic analgesics are judged. It is believed that inhibition of prostaglandin biosynthesis accounts for most of aspirin's anti-flammatory activity and for at least part of its analgesic and antipyretic properties. Aspirin is rapidly absorbed when orally administered and is almost totally hydrolyzed to salicylic acid which has a biologic half-life in the therapeutic plasma concentration range of between six and twelve hours.

It has now been found that the therapeutic composition comprising the combination of an N-monosubstituted-2,2-dialkyl-1,3-propanediol dicarbamate, and aspirin when administered to warm-blooded animals gives relief from pain, muscle spasm and impaired mobility associated with acute muscoloskeletal conditions superior to the effects obtained using the active components separately or from a consideration of the activities of the components of the composition as disclosed in the prior art.

In its broad aspect, the present invention relates to a composition containing a N-monosubstituted-2,2-dialkyl-1,3-propanediol dicarbamate in combination with aspirin.

In a more particular aspect, this invention relates to pharmaceutical compositions, in suitable oral dosage forms, containing approximately one part by weight of an N-monosubstituted-2,2-dialkyl-1,3-propanediol dicarbamate for each two parts by weight of aspirin.

In a further aspect, this invention relates to the use of such compositions for the systematic treatment and control of pain, muscle spasm and limited mobility associated with acute painful muscoloskeletal conditions.

The ratios in which the therapeutically active components are embodied in the preparations of this invention may be varied within rather wide limits. For example, the compositions may contain equal parts by weight of an N-monosubstituted-2,2-dialkyl-1,3-propanediol dicarbamate and aspirin or two or more parts by weight aspirin per part propanediol dicarbamate. The preferred compositions contain approximately two parts by weight aspirin per part N-isopropyl-2-methyl-1,2-propyl-1,3-propanediol dicarbamate.

For administration, the compositions of the invention can be prepared in any of the standard unit dosage forms. Oral administration by the use of tablets and capsules is preferred. Said compositions are prepared in a conventional manner by the addition of suitable pharmaceutical carriers including fillers, diluents, lubricants and the like. When prepared in tablet form, the conventional binding and disintegrating agents are employed. Additional active ingredients compatible with aspirin and propanediol dicarbamate such as appropriate stimulants, sedatives or the like, to add other desirable properties to said compositions. The incorporation of said additives broadens the area of therapeutic utility of the present compositions, making them especially useful in particular cases where, in addition to anti-inflammatory, analgesic and antipyretic activity, other beneficial effects, such as stimulation, sedation, or the like, are desired.

The example which follows is illustrative of a typical composition of the present invention prepared by conventional well known tabletting techniques such as those disclosed in U.S. Pat. Nos. 3,018,221; 2,798,024 and 2,757,124 as a two-layered tablet for oral administration.

EXAMPLE

| INGREDIENT | mg/TABLET |
|---|---|
| LAYER ONE | |
| Carisoprodol | 220.000 |
| Hydroxypropyl Methylcellulose | 5.000 |
| Croscarmellose Sodium, NF, Type A | 10.500 |
| Microcrystalline Cellulose NF | 60.000 |
| Polyvinyl pyrrolidone USP | 11.000 |
| FD & C Red No. 40, Aluminum Lake | 0.100 |

| INGREDIENT | mg/TABLET |
|---|---|
| -continued | |
| FD & C Yellow No. 6, Aluminum Lake | 0.700 |
| Magnesium Stearate, NF | 3.000 |
| Stearic Acid, NF, Powder, Food Grade | 4.300 |
| LAYER TWO | |
| Aspirin 90% Starch Granulation | 340.00 |

What is claimed is:

1. A therapeutic composition, in unit dosage form, for the systematic treatment and relief of pain, muscle spasm and limited mobility associated with acute painful muscoloskeletal conditions, said composition comprising a mixture of from about 1 to about 2 parts by weight aspirin per part by weight of N-propyl-2-methyl-2-propyl-1,3-propanediol dicarbamate.

2. A therapeutic composition as claimed in claim 1 containing 2 parts by weight aspirin, per part by weight N-propyl-2-methyl-2-propyl-1,3-propanediol dicarbamate.

3. A method for systematically treating and relieving pain, muscle spasm and limited mobility associated with acute, painful muscoloskeletal conditions in warm-blooded animals which comprises orally administering to a warm-blooded animal, in need of such treatment, a therapeutic amount of a composition consisting essentially of from about 1 to about 2 parts by weight aspirin, per part by weight N-propyl-2-methyl-2-propyl-1,3-propanediol dicarbamate.

4. A method as claimed in claim 3 wherein said composition contains 2 parts by weight aspirin, per parts by weight N-propyl-2-methyl-2-propyl-1,3-propanediol dicarbamate.

* * * * *